US011772200B2

(12) United States Patent
Stromer et al.

(10) Patent No.: US 11,772,200 B2
(45) Date of Patent: Oct. 3, 2023

(54) ALLOGRAFT OPTIMIZATION SYSTEM

(71) Applicant: Amnio Technology LLC, Phoenix, AZ (US)

(72) Inventors: Merrill Stromer, Phoenix, AZ (US); Larry Macal, Gilbert, AZ (US); Donald R. Taylor, Phoenix, AZ (US); Cris Holmes, Maricopa, AZ (US); James E. Ellis, Tempe, AZ (US)

(73) Assignee: Amnio Technology LLC, Phoenix, AZ (US)

( * ) Notice: Subject to any disclaimer, the term of this patent is extended or adjusted under 35 U.S.C. 154(b) by 70 days.

(21) Appl. No.: 17/515,964

(22) Filed: Nov. 1, 2021

(65) Prior Publication Data

US 2022/0055155 A1    Feb. 24, 2022

Related U.S. Application Data

(63) Continuation of application No. 16/951,790, filed on Nov. 18, 2020, now Pat. No. 11,161,204.
(Continued)

(51) Int. Cl.
*B23K 26/38*    (2014.01)
*A61L 27/36*    (2006.01)
(Continued)

(52) U.S. Cl.
CPC .......... *B23K 26/38* (2013.01); *A61L 27/3691* (2013.01); *B23K 26/082* (2015.10);
(Continued)

(58) Field of Classification Search
CPC ........ A61B 2017/3225; A61L 27/3691; B23K 2103/38; B23K 26/082; B23K 26/0876;
(Continued)

(56) References Cited

U.S. PATENT DOCUMENTS 5,921,980 A    7/1999  Kirn
6,326,019 B1  12/2001  Tseng
(Continued)

FOREIGN PATENT DOCUMENTS

WO    2019084557 A1    5/2019

*Primary Examiner* — Dana Ross
*Assistant Examiner* — Joseph W Iskra
(74) *Attorney, Agent, or Firm* — Invention To Patent Services; Alex Hobson

(57) ABSTRACT

An allograft optimization system utilizes an optical system to determine the outer perimeter of a tissue blank for allograft cutting therefrom. The optical system determines an optimal allograft array pattern that can be derived from the irregular tissue blank and may include a plurality of various allograft shapes and sizes. A computer operates an allograft optimization computer program that receives input regarding the outer perimeter of the tissue blank. A cutting implement, such as a laser, is configured to cut the allografts from the irregularly shaped tissue blank according the allograft array pattern. The cutting implement is automatically actuated by an actuator with respect to the tissue blank to cut the allografts therefrom. The cutting implement may be a laser or a galvo laser that is directed by one or more mirrors. The tissue may be birth tissue including placental tissue and amnion.

20 Claims, 4 Drawing Sheets

Related U.S. Application Data

(60) Provisional application No. 63/008,087, filed on Apr. 10, 2020.

(51) Int. Cl.
  *B23K 26/402* (2014.01)
  *B25J 11/00* (2006.01)
  *B25J 9/16* (2006.01)
  *B25J 13/08* (2006.01)
  *B23K 37/04* (2006.01)
  *B23K 26/082* (2014.01)
  *B25J 9/02* (2006.01)

(52) U.S. Cl.
  CPC ........ *B23K 26/402* (2013.01); *B23K 37/0408* (2013.01); *B25J 9/1664* (2013.01); *B25J 9/1697* (2013.01); *B25J 11/0055* (2013.01); *B25J 13/08* (2013.01); *B25J 9/026* (2013.01)

(58) Field of Classification Search
  CPC .. B23K 26/38; B23K 26/402; B23K 37/0235; B23K 37/0408; B25J 11/0055; B25J 13/08; B25J 9/026; B25J 9/1664; B25J 9/1697; G05B 2219/45196
  USPC ........................................................ 264/400
  See application file for complete search history.

(56) References Cited

U.S. PATENT DOCUMENTS

| | | |
|---|---|---|
| 6,805,694 B2 | 10/2004 | Donitzky |
| 7,494,802 B2 | 2/2009 | Tseng et al. |
| 3,557,581 A1 | 10/2013 | Ngo |
| 10,092,399 B2 | 10/2018 | Dove et al. |
| 10,105,793 B2 * | 10/2018 | Gabriel .................. B23K 26/38 |
| 10,406,259 B2 | 9/2019 | Daniel |
| 2008/0113007 A1 | 5/2008 | Kurihara et al. |
| 2016/0135906 A1 | 5/2016 | Cattin |
| 2020/0138518 A1 * | 5/2020 | Lang ........................ A61B 5/05 |

* cited by examiner

ALLOGRAFT OPTIMIZATION SYSTEM

CROSS REFERENCE TO RELATED APPLICATIONS

This application is a continuation of U.S. patent application Ser. No. 16/951,790, filed on Nov. 18, 2020, which claims the benefit of priority to U.S. provisional patent application No. 63/008,087, filed on Apr. 10, 2020 and entitled Allograft Optimization System; the entirety of which is hereby incorporated by reference.

BACKGROUND OF THE INVENTION

Field of the Invention

The invention relates to an allograft optimization system that utilizes an optical system to determine the outer perimeter of a tissue blank for allograft cutting therefrom.

BACKGROUND

Allografts made from human tissue are used in a wide variety of medical applications. The tissue blanks derived from donors are precious materials and optimization of utilization of this tissue is desired. Tissue blanks often come in irregular shapes. For example, placental tissue is typically irregular shaped as the placental sack is cut open to produce a tissue blank with a wide variety of curved edges. Allografts of varying sizes can be cut from a tissue blank and often an excessive portion of the tissue blank is wasted due to non-optimal cutting of allografts therefrom.

SUMMARY OF THE INVENTION

The invention is directed to an allograft optimization system that utilizes an optical system to determine the outer perimeter of a tissue blank for allograft cutting therefrom. The optical system determines an optimal pattern of allografts that can be derived from the irregular tissue blank. A computer may operate an allograft optimization computer program that receives input regarding the outer perimeter of the tissue blank and produces an optimized allograft array pattern. This optimized allograft array pattern may include allografts from an order log and may include allografts in an allograft array pattern that are the highest priority from the order log; such as being those due first. A cutting implement is configured to cut the allografts from the tissue sample or irregularly shaped tissue blank according the optimized allograft array pattern. A cutting implement may be a laser.

An exemplary tissue blank is tissue that may be irregularly shaped having an irregularly shaped outer perimeter with a plurality of straight-line segments and/or curved segments that form no specific geometric shape. An irregular shape may include curved segments having intersecting radius of curvature or three or more curved segments having different radius of curvature. The irregularly shaped tissue blank includes any tissue from an animal or human including skin, organ tissue, placental tissue including, but not limited to, amnion, chorion, umbilical cord and the like. The allografts cut from the irregularly shaped tissue blank may be used for grafts, such as skin grafts, or may be an implantable graft.

An exemplary cutting implement may produce a jet of water or a beam of light, such as a laser beam. A waterjet may be used and the tissue blank may be placed on a porous cutting tray, whereby the waterjet can pass through the tissue blank and the cutting tray. An exemplary cutting implement may be a laser and the laser may be configured for cutting through the specific type and thickness of tissue. The power output may be configured to cut the allograft from the tissue blank without excess damage to the tissue. A cutting tray may be used for the tissue blank and the laser may be configured to cut through the tissue but not damage the cutting tray. A cutting tray may be portable and may be placed under the cutting implement and then removed from a cutting station for further processing and removal of the cut allografts.

The cutting implement may be moved with respect to the tissue blank to cut the allografts from the tissue blank. For example, the cutting tray and tissue blank thereon, may be moved by a robotic arm or by a gantry system with at least two degrees of motion, with respect to the cutting implement, to cut the allografts. In an exemplary embodiment, the cutting implement is actuated to cut the allografts and may be actuated by a robotic arm, or by a gantry system that moves the cutting implement in two degrees of freedom. The actuator may receive cutting instructions from the allograft optimization computer program or may be directly controlled by the program. The cutting implement may be a laser and the laser may be directed by one or more mirrors, such as a galvo laser. A laser beam emitted by a galvo laser is moved by the positioning of one or more mirrors to direct and move the laser beam as required to cut the allografts from the tissue blank.

An exemplary optical system utilizes a camera that captures a digital photograph of an irregularly shaped tissue blank. The camera may provide a digital map or coordinates of the perimeter of the tissue blank to an allograft optimization computer program. The contrast of the tissue blank and the allograft cutting tray may enable the camera to effectively determine the perimeter shape. A plurality of perimeter retainers may be employed to further enable the camera to determine the outer perimeter. A plurality of perimeter retainers may be configured along the perimeter of the irregularly shaped tissue blank to retain the irregularly shaped tissue blank in place for cutting by the cutting implement. In an exemplary embodiment, the perimeter retainers have a perimeter identifier configured on an identifier end that is recognized by the camera. This distinctive shape, pattern and/or color may be recognized by the camera or the allograft optimization computer program to determine the perimeter shape of the tissue blank. In an exemplary embodiment, the perimeter retainers include a magnet that is attracted to the cutting tray, thereby enabling quick placement of the perimeter retainers along the perimeter of the tissue blank. Note that if a portion of the tissue blank has defects, the perimeter retainers may be configured to exclude this area. Perimeter retainers may be clips, clamps or other retaining devices that are used to secure the tissue blank in place and may be clips that clip the tissue blank to the cutting tray, for example.

An exemplary method of cutting allografts from an irregularly shaped tissue blank includes receiving the tissue blank and preparing it for allograft cutting which may include, cleaning, rinsing, soaking in various solutions including sterilization solutions, cryogenic freezing solutions, pharmaceutical solutions or medicants, and/or therapeutic solutions which may contain organic tissue or particles, such as micronized birth tissue in amniotic fluid, for example. Tissue may swell or change shape upon soaking in or being treated with various solutions and therefore this process may be carried out before the allografts are cut. In addition, a tissue blank may have one or more layers of tissue removed. For example, placental tissue may have chorion removed to produce amniotic tissue allografts.

After the tissue blank is prepared, the tissue blank is placed on a cutting tray and may be retained by perimeter retainers. In an exemplary embodiment, the perimeter retainers have a contact end with a magnet that is attracted to the cutting tray. A cutting tray may be a ferromagnetic material, such as a metal alloy comprising a ferromagnetic metal, and be made out of or include a magnetic material, such as ferritic stainless steels, cobalt, iron, nickel, gadolinium, dysprosium, permalloy, awaruite, wairakite, or magnetite. A cutting tray may have a coating or layer of a ferromagnetic material, such as a nickel coating, for example. In this embodiment, the perimeter retainers may simply be placed along the perimeter of the tissue blank by placing them down onto the tissue blank. Again, if the tissue blank has defective areas, the perimeter retainers may be configured to exclude these areas. The optical system may then scan the tissue and determine the perimeter shape of the tissue blank. This information may be provided to an allograft optimization computer program and an optimized allograft array pattern may be determined by the computer program. The allograft optimization computer program may then provide instruction and/or control the actuator to cut the allografts from the tissue blank. Again, the actuator may move the tissue blank with respect to the cutting implement and in an exemplary embodiment, the cutting implement is a laser that is moved over the tissue blank.

The summary of the invention is provided as a general introduction to some of the embodiments of the invention, and is not intended to be limiting. Additional example embodiments including variations and alternative configurations of the invention are provided herein.

BRIEF DESCRIPTION OF SEVERAL VIEWS OF THE DRAWINGS

The accompanying drawings are included to provide a further understanding of the invention and are incorporated in and constitute a part of this specification, illustrate embodiments of the invention, and together with the description serve to explain the principles of the invention.

Figure 1:
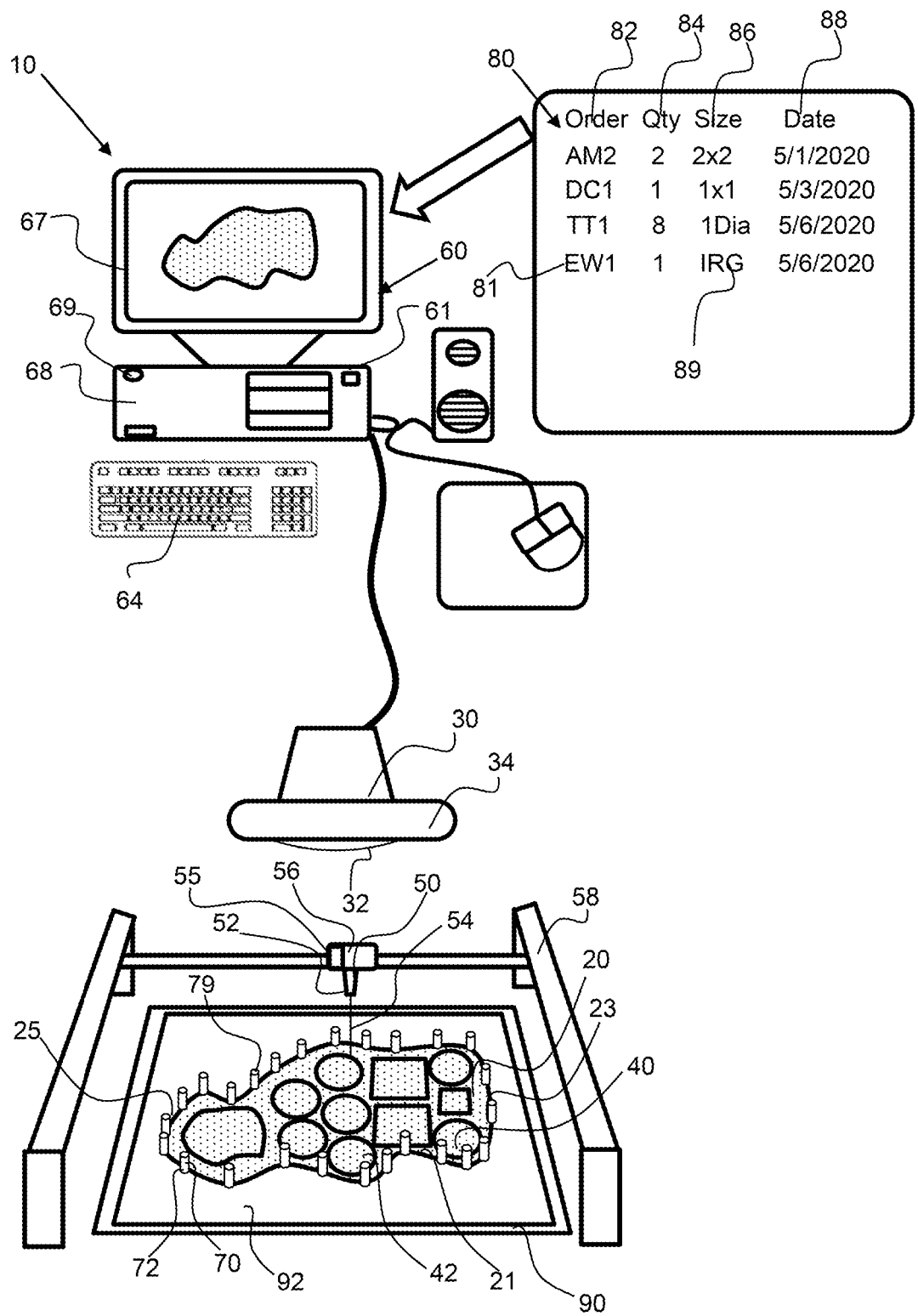
FIG. 1 shows a perspective view of an exemplary allograft optimization system comprising a control system that receives input about a tissue blank shape and size from an optical system and determines an optimal allograft array pattern to be cut from said irregularly shaped tissue blank.

Corresponding reference characters indicate corresponding parts throughout the several views of the figures. The figures represent an illustration of some of the embodiments of the present invention and are not to be construed as limiting the scope of the invention in any manner. Further, the figures are not necessarily to scale, some features may be exaggerated to show details of particular components. Therefore, specific structural and functional details disclosed herein are not to be interpreted as limiting, but merely as a representative basis for teaching one skilled in the art to variously employ the present invention.

DETAILED DESCRIPTION OF THE ILLUSTRATED EMBODIMENTS

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Also, use of "a" or "an" are employed to describe elements and components described herein. This is done merely for convenience and to give a general sense of the scope of the invention. This description should be read to include one or at least one and the singular also includes the plural unless it is obvious that it is meant otherwise.

Certain exemplary embodiments of the present invention are described herein and are illustrated in the accompanying figures. The embodiments described are only for purposes of illustrating the present invention and should not be interpreted as limiting the scope of the invention. Other embodiments of the invention, and certain modifications, combinations and improvements of the described embodiments, will occur to those skilled in the art and all such alternate embodiments, combinations, modifications, improvements are within the scope of the present invention.

As shown in FIG. 1, an exemplary allograft optimization system 10 comprises a control system 60 that receives input to determine a perimeter shape and size for an irregularly shaped tissue blank 21 from an optical system 30 that utilizes a camera 32. The perimeter identifiers 79 are configured on the perimeter retainers 70 that are located around the perimeter of the irregularly shaped tissue blank. The perimeter identifiers are captured by the camera and recognized by the camera or control system. A light 34 may be configured to project light down onto the tissue blank to enable effective recognition of the perimeter identifiers and/or the perimeter of the tissue blank. The perimeter retainers may comprise a magnet 72 that detachably attaches the perimeter retainer to the cutting tray 90, which may comprise a magnetic metal 92. An operator may locate the perimeter retainers around the perimeter of the tissue blank 20 to secure the irregularly shaped tissue blank between the perimeter retainer and the cutting tray.

The irregularly shaped tissue blank 21 is secured to the cutting tray 90 by a plurality of perimeter retainers 70. In an exemplary embodiment, the perimeter retainers comprise a magnet 72 that is attracted to the magnetic metal 92 of the allograft cutting tray 90. The perimeter retainers are positioned around the perimeter 25 of the irregularly shaped tissue blank 21. The perimeter retainers may be configured proximal to either end of a straight segment along the perimeter of an irregularly shaped tissue blank to enable the optical system and computer program to approximate the outer perimeter of the irregularly shaped tissue blank.

The control system may receive input about the perimeter shape and size and then run an optimization program to determine an allograft array pattern 42 to be cut in the irregularly shaped tissue blank. The optimization program may receive an order log 80 input including order identifier 82, order quantity 84, order size 86, and order date 88. An allograft order 81 that has the earliest order date may be prioritized by the optimization program. The allograft order log may include allograft orders 81 for allografts of rectangular shapes, circular or oval shapes or sizes and irregular shapes 89 or sizes. The optimization program 68 may then determine an optimal allograft array pattern 42 to be cut from said tissue blank. A user may use the user interface 64 to input or load the order log and may view the optimal allograft array pattern 42 on the display 67. A user may modify or move an allograft using the user interface 64, such as a mouse, to select an allograft and move it or delete it, as required to avoid any defects in the tissue blank. The allograft array pattern may be automatically updated upon the removal or addition of another allograft by a user. A user may select the allografts from an order log that they want to have cut from the tissue blank and the optimization program may then produce an allograft array pattern that can be displayed on the display. If too many tissue blanks are selected and will not fit on the tissue blank, the computer program may alert the user that they need to eliminate one or more of the allografts from the list. The computer program may also produce an optimal allograft array pattern from the allograft selection leaving some out of the array to enable an optimal usage of the area 23 of the tissue blank 20.

The allografts 40 may then be cut from the irregularly shaped tissue blank 21 by a cutting implement 50, such as a laser 52. A laser beam's 54 intensity and power level may be configured to cut the tissue blank but not cut into or through the cutting tray 90. The cutting implement, or laser, may be moved by an actuator 56 which may be a robotic arm, or a gantry 58 as shown. A gantry may move the laser in two degrees of freedom to enable cutting of allografts that are any shape including rectangular, circular, oval or irregularly shaped or custom shaped. The cutting implement 50, may receiving instructions from the control system 60, or computer program 69 running on a computer 61 that provides actuating instructions for the optimal allograft array pattern 42. As described herein, the laser 52 may be a galvo laser that emits a laser beam 54 that is directed by one or more mirrors 55 to move the laser beam to cut the allografts from the irregularly shaped tissue blank.

Figure 2:
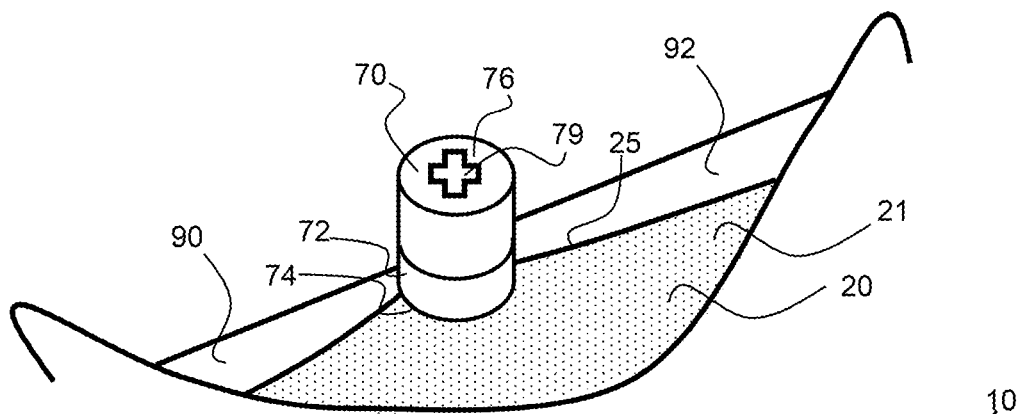
FIG. 2 shows a perspective view of an exemplary perimeter retainer configured along a perimeter of an irregularly shaped tissue blank to secure the tissue blank to the cutting tray, wherein the perimeter retainer has a perimeter identifier on an identifier end.

As shown in FIG. 2, an exemplary perimeter retainer 70 has a magnet 72 on a contact end 74, the end that retains the irregularly shaped tissue blank 21 to the cutting tray 90, and a perimeter identifier 79 on an identifier end 76. As shown, the perimeter retainer is configured proximal to the perimeter 25 of the tissue blank and has the tissue blank 20 retained between the perimeter retainer and the cutting tray. The cutting tray comprises a magnetic material, such as a ferromagnetic metal or metal alloy. The cross shaped identifier on the identifier end 76 of the perimeter retainer may be configured to be recognized by the optical system. The optical system may be configured to recognize this perimeter identifier to enable the computer program to determine the perimeter of the irregularly shaped tissue blank.

Figure 3:
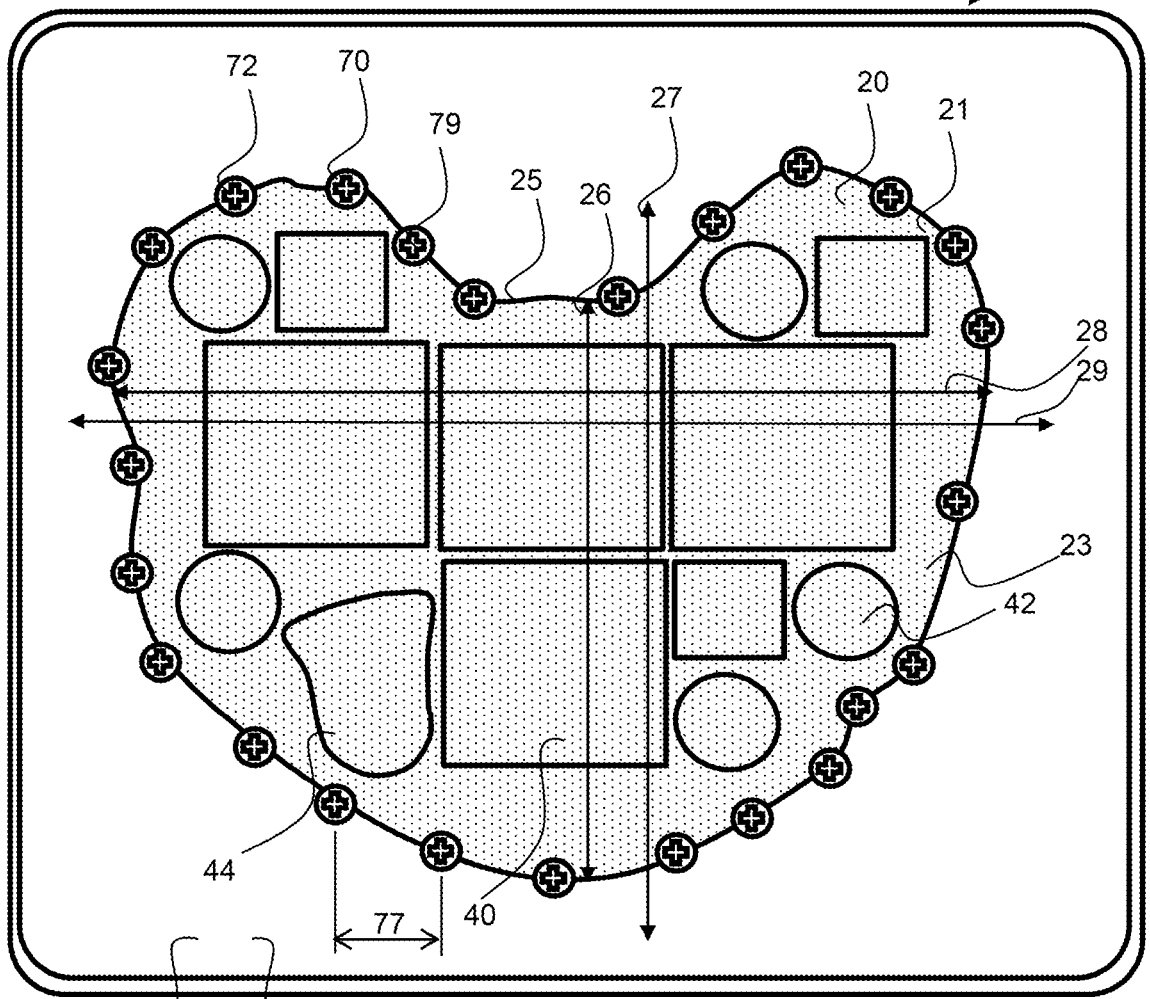
FIG. 3 shows a top view of an exemplary irregularly shaped tissue blank being retained on a cutting tray by perimeter retainers and an optimal allograft array pattern cut therein.

As shown in FIG. 3, a tissue blank 20 forms an irregularly shaped tissue blank 21 having a perimeter 25 that is non-linear and a width 28 that varies non-linearly along the length axis 27. The length 26 also varies non-linearly along a width axis 29. The irregularly shaped tissue blank 21 is retained on the cutting tray 90 by a plurality of perimeter retainers 70. The perimeter retainers comprise a magnet 72 that is attracted to the magnetic metal 92 of the cutting tray 90. The perimeter retainers are configured along the perimeter of the irregularly shaped tissue blank at retainer offset distances 77, which may be uniform or within an upper distance limit. The perimeter retainers may be configured proximal to either end of a substantially linear segment along the perimeter of the tissue blank to enable the optical system and computer program to effectively approximate the outer perimeter shape of the tissue blank.

The optimization program may then determine an allograft array pattern for a plurality of allografts 40 to optimize the usage and yield from the tissue blank. The allografts may be from the order log and may be a regular shape, such as a polygon, circular or an oval shape or custom shaped allografts 44. The optimal allograft array pattern 42 optimizes the area 23 of the tissue blank used for allografts and minimizes the amount of waste from the tissue blank.

Figure 4:
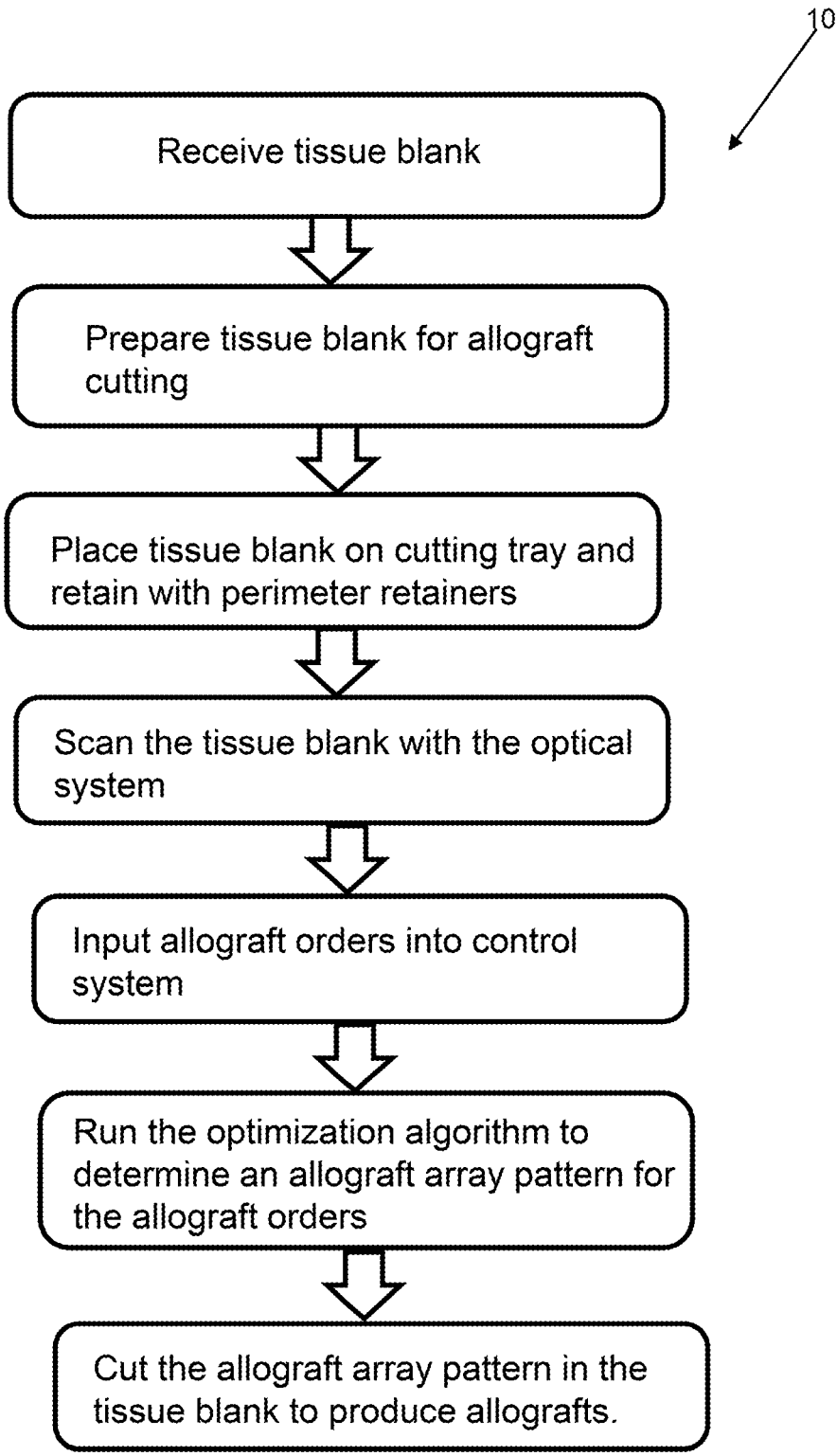
FIG. 4 shows a flowchart of a method to optimize an allograft array pattern in an irregularly shaped tissue blank and cut allografts therefrom.

FIG. 4 shows a flow chart of a method for cutting allograft from an irregularly shaped tissue blank with minimized waste of the tissue blank A tissue blank sample is received, such as placental tissue from a donor. The tissue blank is then prepared for allograft cutting which may include cleaning, rinsing, soaking, sterilizing and the like. The tissue blank is configured on a cutting tray and retained on the cutting tray, such as by perimeter retainers, as described herein. The tissue blank is scanned by the optical system to determine the perimeter shape of the tissue blank. As described herein, the perimeter retainers may comprise a perimeter identifier that is recognized by the optical system. A number of allografts orders are input into a control system and the computer program runs an optimization program or algorithm to determine an optimum allograft array pattern to produce allografts to fulfill the allograft orders. The allografts are then cut from the tissue blank by a cutting implement, such as a laser, to produce a plurality of allografts that fulfill at least some of the allograft orders.

Figure 5:
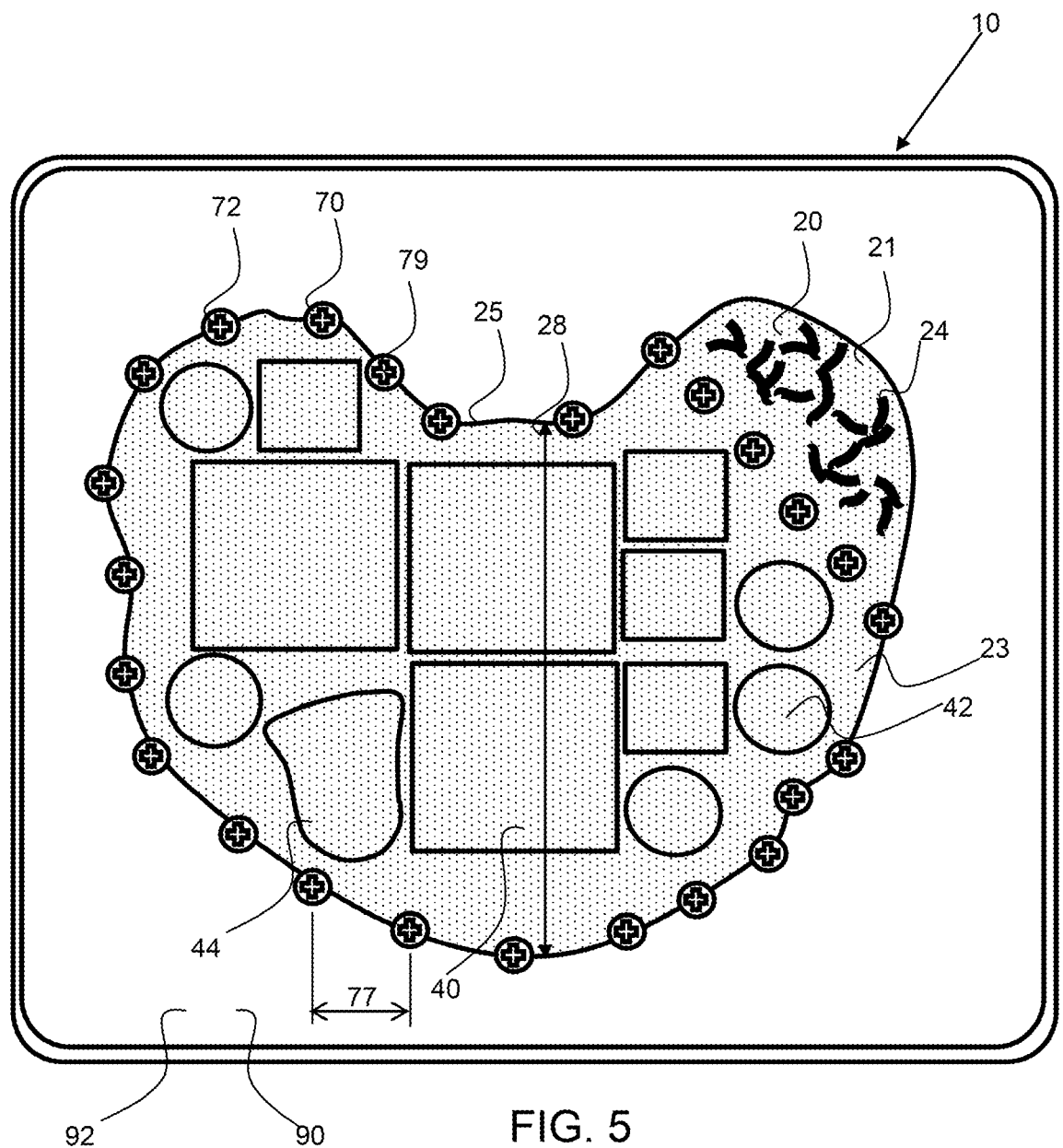
FIG. 5 shows a top view of an exemplary irregularly shaped tissue blank having a defective area and being retained on a cutting tray by perimeter retainers.

As shown in FIG. 5, a tissue blank 20, or tissue from a donor forms an irregularly shape tissue blank 21 having a perimeter 25, that is non-linear, and a surface area 23. The tissue blank has defects 24 and the perimeter retainers 70 are configured to eliminate this defect area for allograft preparation. The irregularly shape tissue blank 21 is retained on the cutting tray 90 by a plurality of perimeter retainers 70. The perimeter retainers comprise a magnet 72 that is attracted to the magnetic metal 92 of the cutting tray 90.

It will be apparent to those skilled in the art that various modifications, combinations and variations can be made in the present invention without departing from the scope of the invention. Specific embodiments, features and elements described herein may be modified, and/or combined in any suitable manner. Thus, it is intended that the present invention cover the modifications, combinations and variations of this invention provided they come within the scope of the appended claims and their equivalents.

What is claimed is:

1. A method of cutting allografts from an irregularly shaped tissue blank comprising:
   a) providing an allograft optimization system comprising:
      i) an optical system configured to determine a perimeter of said irregularly shaped tissue blank; said optical system comprising a camera configured to capture a digital photograph of said irregularly shaped tissue blank;
      ii) a control system comprising:
      an allograft optimization computer program that produces an allograft array pattern;
      a computer configured to operate said allograft optimization computer program;
      iii) a cutting implement;
      iv) an actuator configured to move the cutting implement with respect to the tissue blank;

b) placing said irregularly shaped tissue blank on a cutting tray; said cutting tray comprising a magnetic metal;
c) providing a plurality of perimeter retainers each comprising a magnet;
d) locating said plurality of perimeter retainers along the perimeter of the irregularly shaped tissue blank to retain the irregularly shaped tissue blank in place for cutting by the cutting implement;
   wherein the magnet of the perimeter retainer is attracted to the magnetic metal of the cutting tray to retain the irregularly shaped tissue blank in place on the cutting tray;
e) activating the optical system to determine a perimeter of the irregularly shaped tissue blank; and
   wherein the optical system recognizes the perimeter retainer on the plurality of perimeter retainers to determine said perimeter of the irregularly shaped tissue blank; and
f) cutting said allografts from the tissue blank with said cutting implement via said actuator according to the allograft array pattern.

2. The method of clam 1, wherein the cutting implement is a laser.

3. The method of clam 1, wherein the allograft optimization system further comprises an actuator configured to move the cutting implement to cut the allografts according to the allograft array pattern.

4. The method of clam 3, wherein the actuator is coupled to the computer and configured to receive the allograft array pattern to control the motion of the actuator.

5. The method of clam 4, wherein the actuator is a gantry having two degrees of motion.

6. The method of clam 1, wherein the cutting implement is a galvo laser that emits a laser beam that is actuated by a mirror.

7. The method of clam 1, wherein the tissue blank comprises birth tissue.

8. The method of clam 1, wherein the cutting tray is portable.

9. The method of clam 1, wherein each of the plurality of perimeter retainers comprise a perimeter identifier that is identified by the optical system to determine said perimeter of the irregularly shaped tissue blank.

10. The method of clam 9, wherein the perimeter identifiers is the identifier end of the perimeter retainer.

11. The method of clam 1, further comprising an allograft order log including an allograft size for an allograft order in the allograft order log and wherein the allograft array pattern includes an allograft size from said allograft order log.

12. The method of clam 11, wherein the allograft array pattern includes a plurality of allograft sizes from the allograft order log.

13. The method of clam 12, wherein the allograft array pattern is arranged on the irregularly shaped tissue blank to produce an allograft array pattern including allografts from the allograft order log that have an earliest order date.

14. Method of cutting allografts from an irregularly shaped tissue blank comprising:
a) providing an allograft optimization system comprising:
   i) an optical system configured to determine a perimeter of said irregularly shaped tissue blank; said optical system comprising a camera configured to capture a digital photograph of said irregularly shaped tissue blank;
   ii) a control system comprising:
      an allograft optimization computer program that produces an allograft array pattern;
      a computer configured to operate said allograft optimization computer program;
   iii) a cutting implement;
   iv) an actuator configured to move the cutting implement with respect to the tissue blank;
b) placing said irregularly shaped tissue blank on a cutting tray;
c) providing a plurality of perimeter retainers each comprising a perimeter identifier;
d) locating said plurality of perimeter retainers along the perimeter of the irregularly shaped tissue blank to retain the irregularly shaped tissue blank in place for cutting by the cutting implement;
   wherein the plurality of perimeter retainers retain the irregularly shaped tissue blank in place on the cutting tray;
e) activating the optical system to determine a perimeter of the irregularly shaped tissue blank; and
   wherein the optical system recognizes the perimeter identifier on the plurality of perimeter retainers to determine said perimeter of the irregularly shaped tissue blank; and
f) cutting said allografts from the tissue blank with said cutting implement via said actuator according to the allograft array pattern.

15. He method of clam 14, wherein the perimeter identifiers are configured on the identifier ends of the perimeter retainer.

16. He method of clam 14, wherein the perimeter identifiers are the identifier ends of the perimeter retainer.

17. The method of clam 14, wherein the cutting implement is a laser.

18. The method of clam 14, wherein the tissue blank comprises birth tissue.

19. He method of clam 14, further comprising an allograft order log including an allograft size for an allograft order in the allograft order log and wherein the allograft array pattern includes an allograft size from said allograft order log.

20. The method of clam 19, wherein the allograft array pattern includes a plurality of allograft sizes from the allograft order log.

\* \* \* \* \*